United States Patent [19]
Ward

[11] Patent Number: 4,606,756
[45] Date of Patent: Aug. 19, 1986

[54] HERBICIDAL 2-(NITROGEN HETEROCYCLE)5-AMINO-3-OXO-4-(SUBSTITUTED-PHENYL)-2,3-DIHYDROFURANS

[75] Inventor: Carl E. Ward, San Jose, Calif.

[73] Assignee: Chevron Research Company, San Francisco, Calif.

[21] Appl. No.: 666,074

[22] Filed: Oct. 26, 1984

[51] Int. Cl.$^4$ ............... C07D 401/14; C07D 405/04; A01N 43/08
[52] U.S. Cl. ......................................... 71/94; 71/95; 546/283; 546/281; 546/275; 546/256; 546/208; 546/194; 546/187; 548/517; 548/518
[58] Field of Search ............... 546/283, 281, 193, 194, 546/208, 187, 256, 275; 260/244.4; 71/94

[56] References Cited

U.S. PATENT DOCUMENTS 4,537,623  8/1985  Ward ........................................ 71/90

FOREIGN PATENT DOCUMENTS 42-19090  9/1967  Japan .
44-13710  6/1969  Japan .
1521092   8/1978  United Kingdom .

OTHER PUBLICATIONS

Umio et al., Chem. Abst., 10352e, vol. 69; and Chem. Abst., 61195e, vol. 71, 1969.
Capparo et al., Helvetica Chemica Acta, vol. 66, pp. 362–378, 1983.
Chemiker-Zeitung, 104 (1980), No. 10, pp. 302–303.

Primary Examiner—Jane T. Fan
Attorney, Agent, or Firm—T. G. DeJonghe; L. S. Squires

[57] ABSTRACT

Herbicidal 2-(azaheterocycle)-5-amino-3-oxo-4-(substituted-phenyl)-2,3-dihydrofurans and derivatives thereof. The compounds generally exhibit both pre-emergence and post-emergence phytotoxicity and are useful as herbicides and also plant growth regulating agents at low dosages.

29 Claims, No Drawings

HERBICIDAL 2-(NITROGEN HETEROCYCLE)5-AMINO-3-OXO-4-(SUBSTITUTED-PHENYL)-2,3-DIHYDROFURANS

BACKGROUND OF THE INVENTION

This invention relates to 2-(nitrogen heterocycle) 5-amino-3-oxo-4-(substituted-phenyl)-2,3-dihydrofurans and derivatives thereof and to the use of such compounds as herbicides and plant growth regulators. *Chemiker-Zeitung* 104 (1980) No. 10, Pages 302–303, is an academic paper disclosing the ring closure of 1-(dimethylamino)-2,4-diphenyl-1-buten-3,4-dione to yield 5-dimethylamino-2,4-diphenyl-2,3-dihydrofuran. British Pat. No. 1,521,092, discloses certain 3-phenyl-5-substituted-4(1H)-pyrid-ones or -thiones as herbicides. Japanese Patent Application 13,710/69 (Chemical Abstracts 71:61195e) discloses 5-amino-3-oxo-4-(phenyl or 4-chlorophenyl)-2,3-dihydrofurans. Japanese Patent No. 19090 (Chemical Abstracts 69P10352e) discloses certain 2,3-dihydrothiophenes as pharmaceuticals. *Helvetica Chemica Acta*, Volume 66, Pages 362–378 (1983) discloses 5-N-cyclopropyl-4-phenyl-2-methoxycarbonylmethylene-3-furanone as part of an academic chemical synthesis discussion.

In my copending applications, U.S. Ser. Nos. 505,169 and 607,610, filed June 17, 1983, and May 9, 1984, respectively, and U.S. Ser. No. 594,497, filed Mar. 29, 1984, I disclosed certain 2-substituted-5-amino-3-oxo-4-(substituted phenyl)-2,3-dihydrofuran derivatives and 2-substituted-5-amino-3-oxo-4-(furanyl or thienyl)-2,3-dihydrofuran derivatives, respectively, and their use as herbicides.

SUMMARY OF THE INVENTION

The present invention provides compounds having both pre-emergence and post-emergence herbicidal activity. The compounds have especially good pre-emergence activity against a broad spectrum of both broad-leaf weeds and grassy weeds. At lower application rates the compounds also exhibit plant growth regulating properties.

The compounds of the present invention can be represented by the following generic formula:

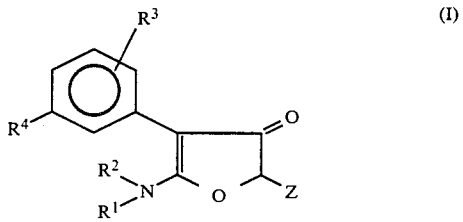

wherein $R^1$ is hydrogen or alkyl having 1 through 4 carbon atoms;

$R^2$ is hydrogen, alkyl having 1 through 4 carbon atoms, alkenyl having 3 or 4 carbon atoms, alkoxycarbonylalkyl having from 1 through 4 carbon atoms in the alkoxy moiety and from 1 through 4 carbon atoms in the alkyl moiety alkoxyalkyl wherein the alkoxy and alkyl moieties independently have 1 through 3 carbon atoms or alkylthioalkyl wherein the alkyl moieties independently have 1 through 3 carbon atoms; or $R^1$ and $R^2$ together with the nitrogen to which they are joined, form a saturated nitrogen heterocycle having from 3- through 6-ring atoms one of which is the joining nitrogen and the remainder of which are carbon atoms or an unsaturated nitrogen heterocycle selected from the group of 2-pyrrolin-1-yl; 3-pyrrolin-1-yl; 1,2,3,4-tetrahydropyrid-1-yl; or 1,2,5,6-tetrahydropyrid-1-yl;

$R^3$ is hydrogen, lower alkyl, lower alkoxy, halo, or trifluoromethyl and can be at any available position on the phenyl ring;

$R^4$ is lower alkyl, lower alkoxy, halo, lower haloalkyl having 1 through 4 carbon atoms and 1 to 3 of the same or different halo atoms; lower haloalkoxy having 1 through 4 carbon atoms and 1 through 3 of the same or different halo atoms; or lower haloalkylthio having 1 through 4 carbon atoms and 1 through 3 of the same or different halo atoms; and Z is a saturated or unsaturated nitrogen heterocycle radical having 5- or 6-ring atoms, one of which is nitrogen, and the remainder of which are carbon atoms, with the proviso that said nitrogen heterocycle is not attached via the two-position of said heterocycle; or Z is an alkyl-substituted saturated or unsaturated nitrogen heterocycle wherein said nitrogen heterocycle is as defined hereinabove but has a methyl or ethyl substituent on the ring nitrogen atom.

The invention also comprises compatible salts of the compound of Formula (I).

The compounds exist as keto-enol tautomer isomers with respect to the 3-keto group shown in Formula I. Also, where the compounds of Formula (I) have an asymmetric carbon atom they can exist as optical isomers. The above formula is intended to encompass both the respective tautomers and optical and geometric isomers where they exist as well as mixtures thereof and the respective isomers as well as mixtures thereof are encompassed within the invention.

It has also been discovered that the presence of a 3-trifluoromethyl substituent on the 4-phenyl group of the compounds of the present invention generally very substantially enhances herbicidal activity.

In a further aspect the invention provides a herbicidal composition comprising a compatible carrier and a herbicidally effective amount of the compounds of Formula (I), or compatible salts thereof, or mixtures thereof.

The present invention also provides a method for preventing or controlling the growth of unwanted vegetation, which comprises treating the growth medium and/or the foliage of such vegetation with a herbicidally effective amount of the compound(s) of Formula (I) and/or compatible salts thereof.

In another aspect, the present invention provides a plant growth regulating composition comprising a compatible carrier and a plant growth regulating amount of the compound of Formula (I), compatible salts of Formula (I), or mixtures thereof, effective to alter the normal growth pattern of said plants.

The present invention also provides a method for regulating plant growth which comprises treating the growth medium and/or the foliage of such vegetation with a plant growth regulating effective amount of the compound(s) of Formula (I) and/or compatible salts thereof, effective to alter the normal growth pattern of said plants.

The present invention also provides chemical intermediates and processes for preparing the compounds of Formula (I).

The invention will be further described hereinbelow.

FURTHER DESCRIPTION OF THE INVENTION AND THE PREFERRED EMBODIMENTS

Illustrations of typical compounds of Formula (I) of the present invention can be had by reference to Examples 1–6 set forth hereinbelow. In terms of substituents, the preferred compounds are those wherein $R^3$ is hydrogen, $R^1$ and $R^2$ are independently hydrogen, methyl, ethyl or n-propyl, and more preferably one of $R^1$ or $R^2$ is hydrogen and the other is hydrogen, methyl, ethyl or n-propyl, preferably methyl or ethyl. Preferably, $R_3$ is hydrogen and $R^4$ *1 is lower haloalkyl, especially trifluoromethyl. When $R^1$* and/or $R^2$ is alkenyl, preferably the alkenyl group has 3 to 4 carbon atoms and Z is preferably pyrid-3-yl; pyrrol-3-yl; N-methylpyrrol-3-yl; N-ethylpyrrol-3-yl.

The compounds of the invention wherein $R^1$ and $R^2$ are each hydrogen can be prepared by the following schematically represented process:

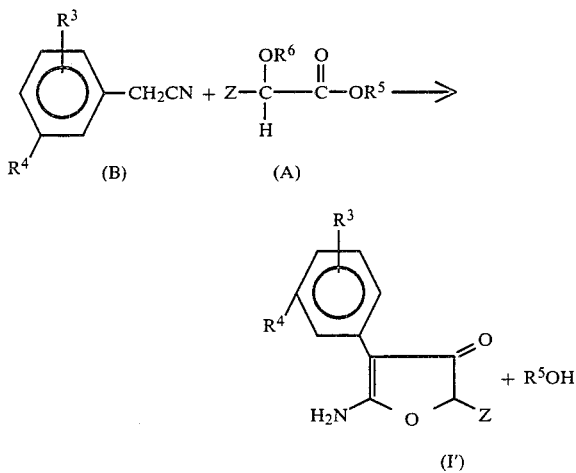

wherein $R^3$, $R^4$, and Z are as defined hereinabove; $R^5$ is lower alkyl (e.g., methyl, ethyl, etc.) aryl (e.g., phenyl, etc.) or arylalkylene (e.g., benzyl, etc.) $R^6$ is hydrogen or an alkali metal cation.

This process can be conveniently effected by contacting Compound (B) with Compound (A), and a strong base (e.g., sodium methoxide, sodium ethoxide), preferably in an inert organic solvent.

Typically, this process is conducted at temperatures in the range of about from 0° to 100° C., preferably 75° to 85° C. for about from 5 to 36 hours, preferably 18 to 24 hours, using about from 1 to 10, preferably 1 to 1.2 moles of Compound (A) per mole of Compound (B).

Suitable strong bases which can be used include, for example, alkali metal alkanolates, for example, sodium methoxide, sodium ethoxide, potassium ethoxide, sodium hydride, potassium hydride, and the like. The strong base should preferably be one which does not yield water as a by-product in this reaction system.

Suitable inert solvents which can be used include, for example, lower alkanols (for example, methanol, ethanol, and propanol) tetrahydrofuran, dimethoxyethane, dioxane, and the like, and compatible mixtures thereof. Conveniently, the alkali metal alkanolate is prepared in situ by reacting an alkali metal with excess alkanol which in turn serves as solvent for the above reaction.

The starting materials of Formula (B) are generally known materials and can be prepared by known procedures, or obvious modifications thereof (i.e., substitution of appropriate starting materials). The preparation of Compound (B) is for example described in Org. Syn. Coll., Volume 1, 107 (1941).

The hydroxy esters of Formula (A) are also generally known compounds and can be prepared by known procedures or by obvious modifications thereof (e.g., by using appropriately substituted starting materials). For example, the hydroxy ester of Formula A, wherein Z is a 6-membered ring saturated or unsaturated heterocycle or a 5-membered ring saturated heterocycle, can be prepared via the following schematically represented process:

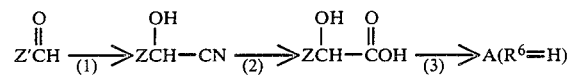

wherein Z' is 6-membered ring atom nitrogen heterocycle, e.g., pyrid-3-yl or a 5-membered ring saturated nitrogen heterocycle.

The first step of this preparation can be effected by contacting the appropriate formyl heterocycle with a cyanide salt (e.g. potassium cyanide) in an aqueous mineral acid (e.g. aqueous hydrochloric acid) at low temperatures in the range of about from −10° C. to 0° C. In the second step of this process the cyanide group is converted to a carboxy group, for example, via treatment with an aqueous mineral acid (e.g., aqueous hydrochloric acid) at about from 80° C. to 150° C., typically at reflux. In the third step, the carboxy acid is esterified to the corresponding ester of Formula A, for example, via treatment with the appropriate alcohol (for example, ethanol, in which case the ethyl ester of Formula A is obtained, i.e., $R^5$ is ethyl) in the presence of an acid catalyst (e.g., conc. sulfuric acid) at temperatures of about from 80° C. to 150° C., conveniently at reflux.

The formyl heterocycles are also generally known compounds and can be prepared via known procedures or obvious modifications thereof.

The alkali metal alkoxide esters of Formula A (i.e., wherein $R^6$ is alkali metal cation) can be prepared via the following schematically represented reaction sequence:

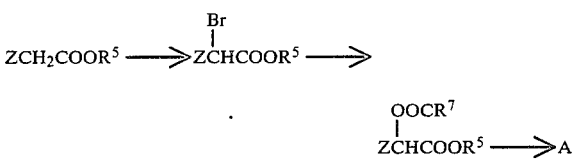

wherein $R^6$=alkali metal) and wherein $R^7$ is alkyl or aryl (preferably methyl or ethyl) and $R^5$ is as defined hereinabove.

The first step in this preparation can be effected by irradiating a mixture of the Z-acetate with N-bromosuccinimide and a catalytic amount of benzoyl peroxide catalyst, preferably in an inert organic solvent, for example, carbon tetrachloride. Typically, this step is conducted at about from 20° to 30° C. for about from 1.0 to 2.0 hours. The second step can be effected by contacting the resulting Z-bromoacetate with an alkali metal ester (e.g., sodium acetate) to yield the corresponding $R^7$ Z-acyloxyacetate. The alkali metal oxides of Formula A can be prepared by treating the Z-acyloxyacetate product with an alkali metal alkoxide (e.g., sodium methoxide) or alkali metal aryloxide preferably in an inert organic solvent, for example, ethanol or dimethylformamide. Typically, this reaction is conducted at temperatures in the range of about from 20° to 30° C. for about from 72 to 96 hours.

The heterocyclic ester starting materials are generally known compounds and can be prepared via known procedures, for example, Org. Syn. Coll. Vol. 3, P. 413 (1955) or obvious modifications thereof.

The starting materials of Formula A wherein Z is a 5-ring atom unsaturated heterocycle, can be prepared by reacting the desired N-trialkylsilanyl heterocycle with an alkyl oxalyl chloride, i.e.,

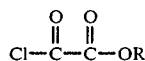

$R = CH_3, CH_2CH_3$ via conventional procedures, preferably in the presence of pyridine, to yield the corresponding 3-alkoxycarbonylcarbonyl-N-trialkylsilanyl heterocycle. (The N-trialkylsilanyl heterocycle starting materials can be prepared via the procedure described in *Tetrahedron Letters* Vol. 24, p. 3455 (1983). The N-trialkylsilanyl group can be cleaved via treatment with tetra-n-butylammonium fluoride in tetrahydrofuran, thus yielding the corresponding alkyl (heterocycle)-oxoacetate. If desired, the ring nitrogen atom can be alkylated at this point, for example, via treatment with alkyl iodide, sodium hydride (base) in tetrahydrofuran. The oxo group can then be reduced, for example via treatment with sodium borohydride, thus yielding the corresponding unsaturated 5-membered ring heterocycle derivative of Formula A.

The compounds of the present invention wherein the Z-heterocycle group is attached via the nitrogen ring atom are best prepared from the corresponding 2-bromo-3-oxo-4-(substituted phenyl)-5-amino-2,3-dihydrofuran derivatives:

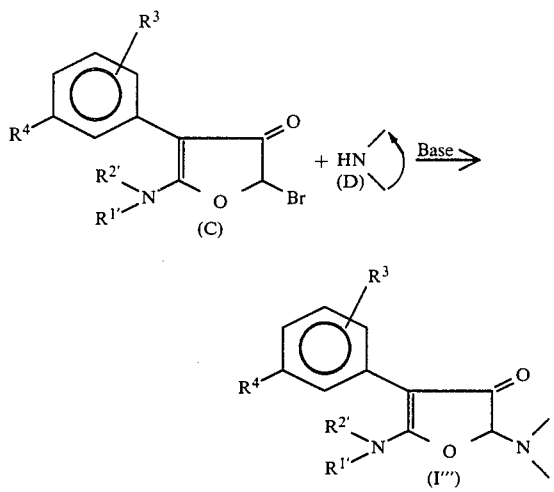

wherein $R^3$ and $R^4$ are as defined hereinabove and $R^{1'}$ and $R^{2'}$ are as defined for $R^1$ and $R^2$, respectively but are not hydrogen.

This reaction can be conveniently effected by contacting compound C with the desired heterocycle D under basic conditions preferably in an inert organic solvent. Typically, this process is conducted at temperatures in the range of about from 0° to 60° C. for about from 1 to 24 hours using about from 0.5 to 2 moles of compound C per mole of compound D. Typically, about from 1 to 2 mole equivalents of base are used per mole of compound (C). Suitable bases which can be used include for example, sodium hydride, tertiary amine, sodium hydroxide, sodium carbonate, excess compound D, and the like. Suitable inert organic solvents which can be used include, for example, methylene chloride, dimethyl formamide, dimethoxyethane, tetrahydrofuran, dioxane, and the like.

The compounds wherein $R^1$ and/or $R^2$ are hydrogen, can be prepared by treating the corresponding compound of Formula I''', with ammonia or a monoalkyl amine, via the procedure described in the commonly assigned application of P. Pomidor, U.S. Ser. No. 666,078 filed on even date herewith, and incorporated herein by reference.

The starting materials of Formula C can be prepared by reacting the corresponding 3-oxo-4-(substituted phenyl)-5-disubstituted amino-2,3-dihydrofuran derivative with N-bromosuccinimide. The 3-oxo-4-(substituted phenyl)-5-amino-2,3-dihydrofuran starting materials can be prepared via the same general procedure as described hereinabove with respect to the preparation of compound I' but replacing starting material A with methyl hydroxyacetate. Further details regarding the preparation of compound C can be had by reference to my copending application U.S. Ser. No.666,075, filed on even date herewith, and incorporated herein by reference.

The compound of Formula (I) wherein one or both of $R^1$ and $R^2$ is other than hydrogen can be prepared by alkylation of the amino group:

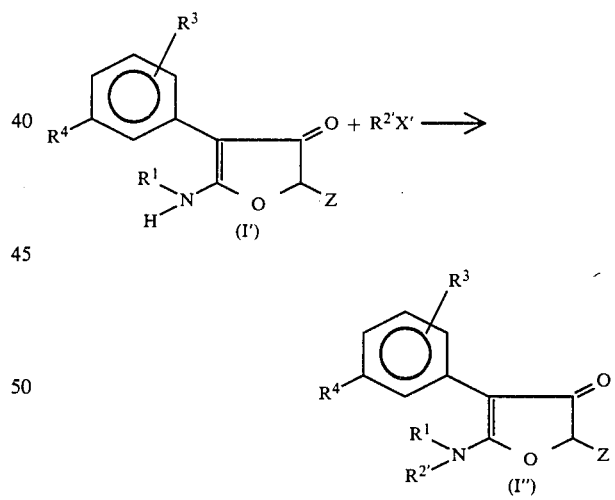

wherein $R^1$, $R^3$, $R^4$ and Z are as defined hereinabove; $R^{2'}$ is as defined for $R^2$ but is not hydrogen; and $R^{2'}X'$ is an alkylation agent.

This process can be effected by contacting Compound (I') with a suitable alkylation agent capable of alkylating primary or secondary amino groups.

For example, this can be effected by contacting Compound (I') with an $R^{2'}$ halide, preferably, chloride, bromide or iodide, preferably in an inert organic solvent and preferably in the presence of a scavenger base. Typically, this process is conducted at temperatures in the range of about from 0° to 100° C., preferably 20° to 45° C. for about from 1.0 to 72.0, preferably 2.0 to 18.0 hours. Where it is desired to only monoalkylate, then typically about from 1.0 to 1.1 moles of $R^{2'}$ halide is used per mole of Compound (I'). Where it is desired to alkylate both amino hydrogens, then typically about from 1.9 to 4.0 moles of $R^{2'}$ halide are used per mole of Compound (I'). In the case where it is desired to prepare the compound wherein $R^{2'}$ is alkoxyalkyl or alkylthioalkyl, it is preferred to use a large excess of $R^{2'}$ halide even where monoalkylation is desired; for example, 3 to 6 moles of $R^{2'}Z''$ per mole of I', compounds wherein $R^1$ and $R^2$ together with the amino nitrogen atoms form a saturated heterocycle can be prepared by using the appropriate halide-$(CH_2)_{2-5}$-halide, wherein $Z''$ is Cl or Br alkylating agent. The $R^1R^2N$ unsaturated heterocycle can be prepared by using the appropriate cis-alkenyl dihalide, wherein one of the halo atoms is in each of the terminal alkenyl carbon. Also variation in $R^1$ and $R^2$ can be effected by first alkylation of only one of the two amino hydrogens and then alkylating the second amino hydrogen with an alkylating agent having a different $R^{2'}$ group.

Suitable inert organic solvents which can be used, include, for example, liquid halogenated alkanes; for example, methylene chloride, carbon tetrachloride, dichloroethane; tetrahydrofuran and the like. Suitable scavenger bases include, for example, the bases described hereinabove with respect to the reaction of Compound (A) with Compound (B).

The compounds of Formula (I") wherein $R^2$ is lower alkyl (e.g., methyl) and $R^1$ is hydrogen or lower alkyl, can be advantageously prepared using dialkyl sulfate as the alkylating agent. This can be conveniently effected by contacting the compound of Formula (I') or (I") with the desired lower alkyl sulfates in the presence of a strong base and preferably in an inert organic solvent in the presence of a phase transfer agent. Typically, this process is conducted at temperatures in the range of about from 0° to 100° C., preferably 20° to 45° C., using about from 1.0 to 4.0 moles of dialkyl sulfate per mole of Compound(I'). An excess, typically about 2.5 mole of base is used. Preferably, this process is also conducted in an inert organic solvent such as, for example, methylene chloride, carbon tetrachloride, dichloroethane, tetrahydrofuran, and the like.

Suitable strong bases which can be used include, for example, sodium hydroxide, potassium hydroxide, sodium ethoxide, sodium carbonate, potassium carbonate, and the like. Suitable phase transfer agents are agents which transfer hydrophilic ions into a lipophilic organic medium and include, for example, benzyl triethylammonium chloride, tetra-n-butylammonium chloride, methyltrioctylammonium chloride, and the like.

The compatible salts of Formula (I) can be prepared by conventional procedures by treating the compound of Formula (I) wherein $R^1$ and/or $R^2$ is hydrogen with a suitable strong base such as, for example, n-butyllithium, sodium hydride, potassium hydride, and the like, having the desired cation, by conventional procedures to replace an amine hydrogen with the desired carbon. The three-position enolite salts can be prepared via further treatment of the amine salt with a base. The enolate salts can be prepared by treating the $R^1$ and/or $R^2$ cation salt with base via conventional procedures. Additional variations in the salt cation can also be effected via ion exchange with an ion exchange resin having the desired cation.

GENERAL PROCESS CONDITIONS

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

DEFINITIONS

As used herein the following terms have the following meanings unless expressly stated to the contrary:

The term "lower alkyl" refers to both straight- and branched-chain alkyl groups having a total of from 1 through 4 carbon atoms. Typical lower alkyls include, for example, methyl, ethyl, n-propyl, isopropyl, n-butyl, t-butyl, and the like.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "halo" refers to the group of fluoro, chloro, bromo and iodo.

The term "alkylene" refers to both straight-chained and branched-chained alkylene groups.

The term "lower alkylene" refers to alkylenes having 1 through 4 carbon atoms, and includes, for example, —$CH_2$; —$CH_2$—$CH_2$—;

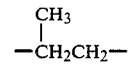

and the like.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl, and the like.

The term "lower alkoxy" refers to the group —OR' wherein R' is lower alkyl.

The term "lower alkylthio" refers to the group —SR' wherein R' is lower alkyl.

The term "lower alkoxyalkyl" refers to the group R'OR"— wherein R' and R" are independently straight-chain or branched-chain alkyl groups having 1 through 3 carbon atoms.

The term "lower alkylthioalkyl" refers to the group R'Sr"— wherein R' and R" re independently straight-chain or branched-chain alkyl groups having 1 through 3 carbon atoms.

The term "lower alkoxycarbonylalkyl" refers to the group $$R'OCR''-\underset{\underset{\|}{O}}{\phantom{R'OCR''}}$$

wherein R' is lower alkyl and R" is alkylene having 1 through 4 carbon atoms and can be straight- or branched-chained. Typical alkoxycarbonylalkyl groups include, for example, —CH₂C(O)OCH₃; —CH(CH₃)-C(O)OC₂H₅, and the like.

The term "lower haloalkyl" refers to haloalkyl compounds having 1 through 4 carbon atoms and 1 through 3 halo atoms independently selected from the group of fluoro, chloro, bromo and iodo. Preferably the lower haloalkyl group has 1 or 2 carbon atoms.

The term "lower haloalkoxy" refers to "lower alkoxy" groups having 1 through 3 halo atoms independently selected from the group of fluoro, chloro, bromo or iodo.

The term "aryl" refers to aryl groups having 6 through 10 carbon atoms and includes, for example, phenyl, naphthyl, indenyl, and the like.

The term "arylalkylene" or "arylalkyl" refers to the group ArR⁵— wherein Ar is aryl and R⁵ is alkylene having 1 through 3 carbon atoms and includes both straight-chained and branched-chained alkylenes, for example, methylene, ethyl, 1-methylethyl, and propyl.

The term "saturated nitrogen heterocycle" as used herein with respect to $R^1$ and $R^2$ of Formula I refers to the groups having the formula:

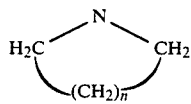

wherein n is 1, 2, or 3.

The terms "saturated nitrogen heterocycle", "alkyl substituted saturated nitrogen heterocycle", as used herein with respect to the Z substituent of Formula I include, for example, groups having the formulas:

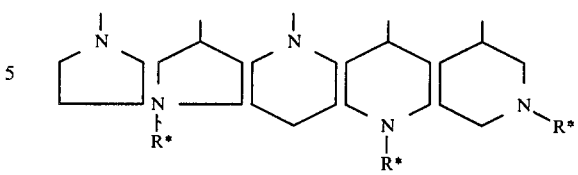

wherein R* is hydrogen, methyl or ethyl.

The terms "unsaturated nitrogen heterocycle" and "alkyl substituted unsaturated nitrogen heterocycle" as used herein with respect to the Z substituent of Formula I, include groups, such as, for example, those having the formulas:

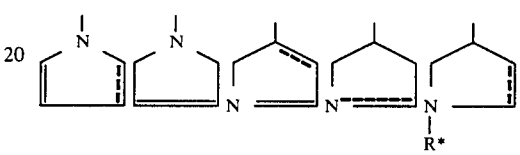

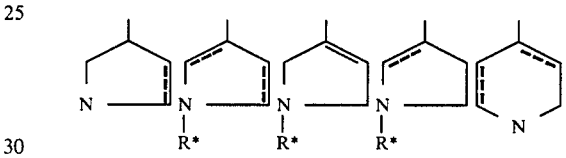

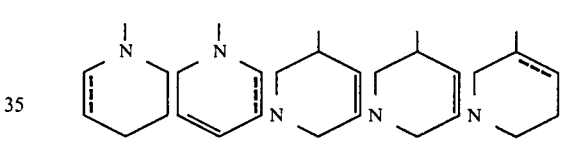

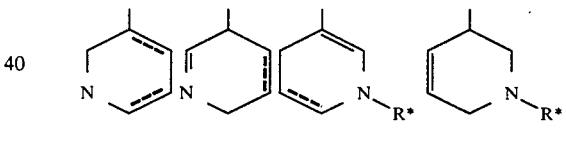

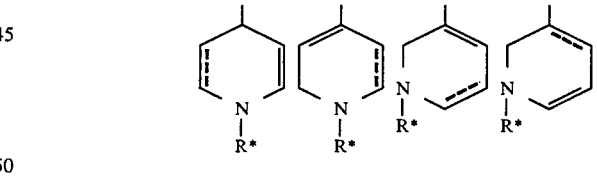

and the like; wherein R* is methyl or ethyl and the dashed bond line $\equiv\equiv\equiv$ indicates a single bond or a double bond.

The term "compatible salts" refers to salts which do not significantly alter the herbicidal properties of the parent compound. Suitable salts include cation salts such as, for example, the cation salts of lithium, sodium, potassium, alkali earth metals, ammonia, quaternary ammonium salts, and the like.

The term "room temperature" or "ambient temperature" refers to about 20°–25° C.

UTILITY

The compounds of Formula (I) exhibit both pre-emergence and post-emergence herbicidal activity and exhibit especially good pre-emergence herbicidal activity.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound or otherwise enhance soil stability.

The composition can also contain various compatible adjuvants, stabilizers, conditioners, insecticides, fungicides, and if desired, other herbicidally active compounds.

At reduced dosages the compounds of the present invention also exhibit plant growth regulating activity and can be used to alter the normal growth pattern of green plants.

The compounds of Formula (I) can be applied as plant growth regulators in pure form, but more pragmatically, as in the case of herbicidal application, are applied in combination with a carrier. The same types of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005 to 90 wt. % of the compound(s) of Formula (I) depending on whether the composition is intended to be applied directly or diluted first.

A further understanding of the invention can be had in the following non-limiting Preparations and Examples. Wherein, unless expressly stated to the contrary, all temperatures and temperature ranges refer to the Centigrade system and the term "ambient" or "room temperature" refers to about 20°–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary, examples are repeated to provide additional starting material for subsequent examples.

PREPARATIONS AND EXAMPLES

Preparation 1

Pyrid-3-yl-Cyanohydrin

In this example 190 ml of aqueous 20% (wt) potassium cyanide solution was slowly added to a stirred mixture containing 48.4 g of 3-formylpyridine in 210 ml of 2M aqueous hydrochloric acid at −5° C. The mixture was maintained at −5° C. overnight (about 15 hours) affording a crystalline product. This product was collected by filtration affording 30.1 g of the title compound.

Preparation 2

Pyrid-3-yl-Hydroxyacetic Acid

In this example a mixture containing 30.1 g of pyrid-3-yl cyanohydrin in 110 ml of concentrated hydrochloric acid was refluxed overnight (about 15 hours) and then evaporated. The residue was dissolved in water and then evaporated. The residue was triturated with acetone and then collected affording 35 g of the title compound.

Preparation 3

Ethyl Pyrid-3-ylhydrdoxyacetate

In this example 35 g of pyrid-3-ylhydroxyacetic acid was admixed with 125 ml of anhydrous ethanol to which 2.5 ml of concentrated sulfuric acid had been added. The mixture was refluxed for 18 hours and then evaporated to remove excess ethanol. The residue was treated with saturated aqueous sodium carbonate solution until basic and then extracted with methylene chloride. The combined methylene extracts were dried over magnesium sulfate and then evaporated to dryness affording 19.3 g of the title compound.

EXAMPLE 1

2-(Pyrid-3-yl)-3-oxo-4-(3-trifluoromethylphenyl)-5-amino-2,3-dihydrofuran

In this example 23 g of sodium was dissolved in 150 ml of ethanol and heated to reflux. A mixture containing 19.7 g of 3'-trifluoromethylphenylacetonitrile and 19.3 g of ethyl pyrid-3-ylhydroxyacetate was added slowly to the refluxing solution and then refluxed overnight (about 16 hours). The mixture was diluted with water, washed with petroleum ether, acidified with aqueous 10% wt. hydrochloric acid and extracted with ethyl ether. The organic phase was separated and dried over magnesium sulfate and evaporated to dryness. The residue was dissolved in ethyl ether, neutralized by washing with saturated aqueous sodium bicarbonate solution and evaporated to dryness. The residue was chromatographed over silica eluting with ethyl acetate. The fractions were combined, washed with an aqueous 10 wt. % sodium carbonate solution, dried over magnesium sulfate and evaporated to dryness. The residue was triturated with 30% vol. ethyl acetate: 70% petroleum ethers.

Similarly, by applying the above-described procedure using the appropriate (substituted phenyl) acetonitrile starting materials, the following compounds can also be prepared:

2-(pyrid-3-yl)-3-oxo-4-(5-chloro-3-trifluoromethylphenyl)-5-amino-2,3-dihydrofuran;
2-(pyrid-3-yl)-3-oxo-4-(4-chloro-3-trifluoromethylphenyl)-5-amino-2,3-dihydrofuran;
2-(pyrid-3-yl)-3-oxo-4-(2-bromo-3-trifluoromethylphenyl)-5-amino-2,3-dihydrofuran;
2-(pyrid-3-yl)-3-oxo-4-(6-fluoro-3-trifluoromethylphenyl)-5-amino-2,3-dihydrofuran;
2-(pyrid-3-yl)-3-oxo-4-(4-methyl-3-trifluoromethylphenyl)-5-amino-2,3-dihydrofuran;
2-(pyrid-3-yl)-3-oxo-4-(5-methoxy-3-trifluoromethylphenyl)-5-amino-2,3-dihydrofuran;
2-(pyrid-3-yl)-3-oxo-4-(6-butoxy-3-trifluoromethylphenyl)-5-amino-2,3-dihydrofuran;
2-(pyrid-3-yl)-3-oxo-4-(3,5-di-trifluoromethylphenyl)-5-amino-2,3-dihydrofuran;
2-(pyrid-3-yl)-3-oxo-4-(3-ethylthiomethylphenyl)-5-amino-2,3-dihydrofuran;
2-(pyrid-3-yl)-3-oxo-4-(3-tribromomethylphenyl-5-amino-2,3-dihydrofuran;
2-(pyrid-3-yl)-3-oxo-4-(3-fluorophenyl-5-amino-2,3-dihydrofuran;
2-(pyrid-3-yl)-3-oxo-4-(3-trifluoromethoxyphenyl-5-amino-2,3-dihydrofuran;
2-(pyrid-3-yl)-3-oxo-4-(3-iodophenyl-5-amino-2,3-dihydrofuran; and
2-(pyrid-3-yl)-3-oxo-4-(2-chloro-3-methylphenyl-5-amino-2,3-dihydrofuran;
2-(pyrid-3-yl)-3-oxo-4-(4-ethyl-3-methylphenyl-5-amino-2,3-dihydrofuran;
2-(pyrid-3-yl)-3-oxo-4-(5-methoxy-3-dichloromethylphenyl-5-amino-2,3-dihydrofuran;
2-(pyrid-3-yl)-3-oxo-4-[5-(1-methylthiopropyl)-3-chlorophenyl]-5-amino-2,3-dihydrofuran;
2-(pyrid-3-yl)-3-oxo-4-(3,5-diethoxyphenyl)-5-amino-2,3-dihydrofuran;
2-(pyrid-3-yl)-3-oxo-4-(3-bromophenyl)-5-amino-2,3-dihydrofuran;
2-(pyrid-3-yl)-3-oxo-4-(3-chloro-4-methylphenyl)-5-amino-2,3-dihydrofuran;
2,-(pyrid-3-yl)-3-oxo-4-(3-bromo-2-ethylphenyl)-5-amino-2,3-dihydrofuran;
2-(pyrid-3-yl)-3-oxo-4-(3,6-dimethylphenyl)-5-amino-2,3-dihydrofuran;
2-(pyrid-3-yl)-3-oxo-4-(3-iodo-4-methylphenyl)-5-amino-2,3-dihydrofuran;
2-(pyrid-3-yl)-3-oxo-4-(3-chlorophenyl)-5-amino-2,3-dihydrofuran;
2-(pyrid-3-yl)-3-oxo-4-(3-triflfuoromethylthiophenyl)-5-amino-2,3-dihydrofuran;
2-(pyrid-3-yl)-3-oxo-4-(3-butylphenyl)-5-amino-2,3-dihydrofuran;
2-(pyrid-3-yl)-3-oxo-4-(3-butoxyphenyl)-5-amino-2,3-dihydrofuran; and
2-(pyrid-3-yl)-3-oxo-4-(3-methylthiophenyl)-5-amino-2,3-dihydrofuran;
2-(pyrid-3-yl)-3-oxo-4-(3-bromophenyl)-5-amino-2,3-dihydrofuran;
2-(pyrid-3-yl)-3-oxo-4-(3-iodo-5-trifluoromethylphenyl)-5-amino-2,3-dihydrofuran;
2-(pyrid-3-yl)-3-oxo-4-(3-propylphenyl)-5-amino-2,3-dihydrofuran;
2-(pyrid-3-yl)-3-oxo-4-(3-methoxyphenyl)-5-amino-2,3-dihydrofuran;
2-(pyrid-3-yl)-3-oxo-4-(3-fluoro-4-trifluoromethylphenyl)-5-amino-2,3-dihydrofuran; and
2-(pyrid-3-yl)-3-oxo-4-(3-propoxyphenyl)-5-amino-2,3-dihydrofuran.

Similarly, by applying the above procedure, using the appropriate (substituted phenyl)acetonitrile and the appropriate ethyl hydroxyacetate heterocycle corresponding heterocycle analogs of the above compounds can also be prepared, for example:

2-(2-pyrrolin-3-yl)-3-oxo-4-(3-trifluoromethylphenyl)-5-amino-2,3-dihydrofuran;
2-(2-pyrrolin-3-yl)-3-oxo-4-(3-trifluoromethylphenyl)-5-amino-2,3-dihydrofuran;
2-(pyrrol-3-yl)-3-oxo-4-(3-trifluoromethylphenyl)-5-amino-2,3-dihydrofuran;
2-(pyrrolidin-3-yl)-3-oxo-4-(3-trifluoromethylphenyl)-5-amino-2,3-dihydrofuran;
2-(N-methylpyrrolidin-3-yl)-3-oxo-4-(3-trifluoromethylphenyl)-5-amino-2,3-dihydrofuran;
2-(N-ethylpyrrol-3-yl)-3-oxo-4-(3-trifluoromethylphenyl)-5-amino-2,3-dihydrofuran;
2-(2-N-methylpyrrol-3-yl)-3-oxo-4-(3-trifluoromethylphenyl)-5-amino-2,3-dihydrofuran;
2-(2H-pyrrol-3-yl)-3-oxo-4-(3-trifluoromethylphenyl)-5-amino-2,3-dihydrofuran;
2-(4-piperidino)-3-oxo-4-(3-trifluoromethylphenyl)-5-amino-2,3-dihydrofuran;
2-(3-piperidino)-3-oxo-4-(3-trifluoromethylphenyl)-5-amino-2,3-dihydrofuran;
2-(1H,4H-pyrid-3-yl)-3-oxo-4-(3-trifluoromethylphenyl)-5-amino-2,3-dihydrofuran;
2-(1H,3H,4H-pyrid-3-yl)-3-oxo-4-(3-trifluoromethylphenyl)-5-amino-2,3-dihydrofuran;
2-(pyrid-4-yl)-3-oxo-4-(3-trifluoromethylphenyl)-5-amino-2,3-dihydrofuran;
2-(2H,5H-pyrid-3-yl)-3-oxo-4-(3-trifluoromethylphenyl)-5-amino-2,3-dihydrofuran;
2-(N-methyl-3-piperidino)-3-oxo-4-(3-trifluoromethylphenyl)-5-amino-2,3-dihydrofuran;
2-(1H,4H-N-ethylpyrid-3-yl)-3-oxo-4-(3-trifluoromethylphenyl)-5-amino-2,3-dihydrofuran;
2-(N-methylpyrid-3-yl)-3-oxo-4-(3-trifluoromethylphenyl)-5-amino-2,3-dihydrofuran;

2-(1H,4H,5H,6H,-N-ethylpyrid-3-yl)-3-oxo-4-(3-trifluoromethylphenyl)-5-amino-2,3-dihydrofuran;
2-(1H,2H,5H,6H-N-methylpyrid-4-yl)-3-oxo-4-(3-trifluoromethylphenyl)-5-amino-2,3-dihydrofuran; etc.

EXAMPLE 2

2-(Pyrid-3-yl)-3-oxo-4-(3-trifluoromethylphenyl)-5-methylamino-2,3-dihydrofuran

Two (2) grams of 2-(pyrid-3-yl)-3-oxo-4-(3-trifluoromethylphenyl)-5-amino-2,3-dihydrofuran was dissolved in 50 ml of methylene chloride at room temperature. 0.24 g of sodium hydroxide, dissolved in the minimum amount of water needed to dissolve the sodium hydroxide, and 0.46 g of benzyltrimethylammonium chloride was added. Then a solution containing 0.79 g of dimethylsulfate in about 10 ml of methylene chloride was slowly added and the mixture stirred for two days at room temperature. The mixture was then washed with water, dried over magnesium sulfate and evaporatyed to a solid residue. The residue was triturated with 30% vol. ethyl acetate: 70% petroleum ether and filtered.

The above preparation was repeated using twice the amount of materials and the preciitates and residues frm the evaporated filtrates from both preparatons were combined and then triturated with acetone affording the title compound as a solid.

Similarly, by applying the above-described procedure to the products listed in Example 1, the corresponding methylamino homologs thereof can be prepared, for example:

2-(pyrid-3-yl)-3-oxo-4-(5-chloro-3-trifluoromethylphenyl)-5-methylamino-2,3-dihydrofuran;
2-(pyrid-3-yl)-3-oxo-4-(4-chloro-3-trifluoromethylphenyl)-5-methylamino-2,3-dihydrofuran;
2-pyrid-3-yl)-3-oxo-4-(2-bromo-3-triflfuoromethylphenyl)-5-methylamino-2,3-dihydrofuran;
2-(pyrid-3-yl)-3-oxo-4-(6-fluoro-3-trifluoromethylphenyl)-5-methylamino-2,3-dihydrofuran;
2-(pyrid-3-yl)-3-oxo-4-(4-methyl-3-trifluoromethylphenyl)-5-methylamino-2,3-dihydrofuran;
2-(pyrid-3-yl)-3-oxo-4-(5-methoxy-3-trifluoromethylphenyl)-5-methylamino-2,3-dihydrofuran;
2-(pyrid-3-yl)-3-oxo-4-(6-butoxy-3-trifluoromethylphenyl)-5-methylamino-2,3-dihydrofuran;
2-(pyrid-3-yl)-3-oxo-4-(3,5-di-trifluoromethylphenyl)-5-methylamino-2,3-dihydrofuran;
2-(pyrid-3-yl)-3-oxo-4-(3-ethylthiomethylphenyl)-5-methylamino-2,3-dihydrofuran;
2-pyrid-3-yl)-3-oxo-4-(3-tribromomethylphenyl)-5-methylamino-2,3-dihydrofuran;
2-(pyrid-3-yl)-3-oxo-4-(3-fluorophenyl9-5-methylamino-2,3-dihydrofuran;
2-(pyrid-3-yl)-3-oxo-4-(3-trifluoromethoxyphenyl)-5-methylamino-2,3-dihydrofuran;
2-(pyrid-3-yl)-3-oxo-4-(3-iodophenyl)-5-methylamino-2,3-dihydrofuran; and
2-(pyrid-3-yl)-3-oxo-4-(2-chloro-3-methylphenyl)-5-methylamino-2,3-dihydrofuran;
2-(pyrid-3-yl)-3-oxo-4-(4-ethyl-3-methylphenyl)-5-methylamino-2,3-dihydrofuran;
2-(pyrid-3-yl)-3-oxo-4-(5-methoxy-3-dichloromethylphenyl)-5-methylamino-2,3-dihydrofuran;
2-(pyrid-3-yl)-3-oxo-4-[5-(1-methylthiopropyl)-3-chlorophenyl]-5-methylamino-2,3-dihydrofuran;
2-(pyrid-3-yl)-3-oxo-4-(3,5-diethoxyphenyl)-5-methylamino-2,3-dihydrofuran;
2-(pyrid-3-yl)-3-oxo-4-(3-bromophenyl)-5-methylamino-2,3-dihydrofuran;
2-(pyrid-3-yl)-3-oxo-4-(3-chloro-4-methylphenyl)-5-methylamino-2,3-dihydrofuran;
2-(pyrid-3-yl)-3-oxo-4-(3-bromo-2-ethylphenyl)-5-methylamino-2,3-dihydrofuran;
2-(pyrid-3-yl)-3-oxo-4-(3,6-dimethylphenyl)-5-methylamino-2,3-dihydrofuran;
2-(pyrid-3-yl)-3-oxo-4-(3,6-dimethylphenyl)-5-methylamino-2,3-dihydrofuran;
2-(pyrid-3-yl)-3-oxo-4-(3-iodo-4-methylphenyl)-5-methylamino-2,3-dihydrofuran;
2-(pyrid-3-yl)-3-oxo-4-(3-chlorophenyl)-5-methylamino-2,3-dihydrofuran;
2-(pyrid-3-yl)-3-oxo-4-(3-trifluoromethylthiophenyl)-5-methylamino-2,3-dihydrofuran;
2-(pyrid-3-yl)-3-oxo-4-(3-butylphenyl)-5-methylamino-2,3-dihydrofuran;
2-(pyrid-3-yl)-3-oxo-4-(3-butoxyphenyl)-5-methylamino-2,3-dihydrofuran; and
2-(pyrid-3-yl)-3-oxo-4-(3-methylthiophenyl)-5-methylamino-2,3-dihydrofuran;
2-(pyrid-3yl)-3-oxo-4-(2-iodo-3-bromophenyl)-5-methylamino-2,3-dihydrofuran;
2-(pyrid-3-yl)-3-oxo-4-(3-iodo-5-trifluoromethylphenyl)-5-methylamino-2,3-dihydrofuran;
2-(pyrid-3-yl)-3-oxo-4-(3-propylphenyl)-5-methylamino-2,3-dihydrofuran;
2-(pyrid-3-yl)-3-oxo-4-(3-methoxyphenyl)-5-methylamino-2,3-dihydrofuran;
2-(pyrid-3-yl)-3-oxo-4-(3-fluoro-4-trifluoromethylphenyl)-5-methylamino-2,3-dihydrofuran;
2-pyrid-3-yl)-3-oxo-4-(3-propoxyphenyl)5-methylamino-2,3-dihydrofuran;
2-(pyrrolidin-1-yl)-3-oxo-4-(3-trifluoromethylphenyl)-5-methylamino-2,3-dihydrofuran;
2-(2-pyrrolin-3-yl)-3-oxo-4-(3-trifluoromethylphenyl)-5-methylamino-2,3-dihydrofuran;
2-(pyrrol-3-yl)-3-oxo-4-(3-trifluoromethylphenyl)-5-methylamino-2,3-dihydrofuran;
2-(pyrrolidin-3-yl)-3-oxo-4-(3-trifluoromethylphenyl)-5-methylamino-2,3-dihydrofuran;
2-(N-methylpyrrolidin-3-yl)-3-oxo-4-(3-trifluoromethylphenyl)-5-methylamino-2,3-dihydrofuran;
2-(pyrrol-1-yl)-3-oxo-4-(3-trifluoromethylphenyl)-5-methylamino-2,3-dihydrofuran;
2-(N-ethylpyrrol-3-yl)-3-oxo-4-(3-trifluoromethylphenyl)-5-methylamino-2,3-dihydrofuran;
2-(2-N-methylpyrrol-3-yl)-3-oxo-4-(3-trifluoromethylphenyl)-5-methylamino-2,3-dihydrofuran;
2-(2H-pyrrol-3-yl)-3-oxo-4-(3-trifluoromethylphenyl)-5-methylamino-2,3-dihydrofuran;
2-(4-piperidino)-3-oxo-4-(3-trifluoromethylphenyl)-5-methylamino-2,3-dihydrofuran;
2-(N-piperidino)-3-oxo-4-(3-trifluoromethylphenyl)-5-methylamino-2,3-dihydrofuran;
2-(1H,4H-pyrid-3-yl)-3-oxo-4-(3-trifluoromethylphenyl)-5-methylamino-2,3-dihydrofuran;
2-(1H,3H,4H-pyrid-3-yl)-3-oxo-4-(3-trifluoromethylphenyl)-5-methylamino-2,3-dihydrofuran;
2-(pyrid-4-yl)-3-oxo-4-(3-trifluoromethylphenyl)-5-methylamino-2,3-dihydrofuran;
2-(2H,5H-pyrid-3-yl)-3-oxo-4-(3-trifluoromethylphenyl)-5-methylamino-2,3-dihydrofuran;
2-(N-methyl-1-piperidino)-3-oxo-4-(3-trifluoromethylphenyl)-5-methylamino-2,3-dihydrofuran;
2-(1H,4H-N-ethylpyrid-3-yl)-3-oxo-4-(3-trifluoromethylphenyl)-5-methylamino-2,3-dihydrofuran;

2-(N-methylpyrid-3-yl)-3-oxo-4-(3-trifluoromethyl-
phenyl)-5-methylamino-2,3-dihydrofuran;
2-(1H,4H,5H,6H-N-ethylpyrid-3-yl)-3-oxo-4-(3-tri-
fluoromethylphenyl)-5-methylamino-2,3-dihydrofu-
ran;
2-(1H,2H,5H,6H-N-methylpyril-4-yl)-3-oxo-4-(3-tri-
fluoromethylphenyl)-5-methylamino-2,3-dihydrofu-
ran; etc.

Similarly, by approximately doubling the amount of dimethylsulfate and increasing the reaction time, the corresponding 5-dimethylamino homologs of the above compounds can be prepared. Similarly, by using diethylsulfate in place of dimethylsulfate, the corresponding 5-ethylamino and 5-diethylamino homologs of the above compounds can be prepared.

EXAMPLE 3

2-(Pyrrol-1-yl-)-3-oxo-4-(3-trifluoromethylphenyl)-5-dimethylamino-2,3-dihydrofuran In this example, 1.05 g of pyrrole dissolved in 10 ml of dimethylformamide was slowly added to an anhydrous slurry containing 0.76 g of sodium hydride (added as a 50% in oil mixture) in 25 ml of dimethylformamide at room temperature. After the addition was completed and evolution of hydrogen observed to cease a solution containing 5 g of 2-bromo-3-oxo-4-(3-trifluoromethyl-phenyl)-5-dimethylamino-2,3-dihydrofuran in 25 ml of dimethylformamide was added dropwise. The mixture was then stirred for 48 hours at room temperature. The mixture was then sampled and examined by thin layer chromatography and then heated at 65° C. for one-half hour. The mixture was then poured into water, then acidified to about pH 1 by the addition of aqueous 10 wt.% hydrochloric acid. The mixture was extracted three times with ethyl ether. The combined extracts were washed three times with aqueous saturated sodium chloride solution, dried over magnesium sulfate and then evaporated in vacuo yielding a dark oil. The oil was chromatographed by high-pressure liquid chromatography over silica gel eluting with 1:1 vol. petroleum ether-ethyl acetate yielding the title compound.

EXAMPLE 4

2-(Pyrid-3-yl)-3-oxo-4-(3-trifluoromethylphenyl)-5-allylamino-2,3-dihydrofuran

This example illustrates a preparation which can be used to prepare the 5-allylamino substituted compounds of the invention.

One gram of sodium hydroxide in 4.0 ml of water is added to a mixture of 0.32 g (1 mmole) of 2-pyrid(-3-yl)-3-oxo-4-(3-trifluoromethylphenyl)-5-amino-2,3-dihydrofuran in 80 ml of methylene chloide at room temperature followed by the addition of 1 mmol of allyl brmide and 0.27 g of benzyltriethylammonium chloride. The resulting mixture is stirred at room temperature for about 18 hours after which time it can be washed three times with water, dried over magnesium sulfate and concentrated in vacuo. The residue can be purified by chromatography over silica gel to yield the title compound.

Similarly, by applying this procedure to the products listed in Examples 1 and 2, the corresponding 5-allylamino analogs thereof can be prepared. Similarly, by approximately doubling the amount of allyl bromide and sodium hydroxide, the corresponding 5-dial-lylamino analogs thereof can be prepared.

In a like manner, by using ethyl bromide in place of allyl bromide, the corresponding 5-ethyl and 5-diethyl analogs can be prepared and by using the 5-methylamino analogs of Example 3 as starting materials, the corresponding 5-N-methyl-N-allylamino and 5-N-methyl-N-ethyl analogs can be prepared.

Similarly, by following the same procedure by respectively using methoxymethyl bromide, ethylthiomethyl bromide, methyl bromoacetate, methyl 2-bromobutyrate, 1,5-dibromopentane, and cis-1,4-dibromobut-1-ene in place of alkyl bromide the corresponding 5-methoxymethylamino, 5-ethylthiomethylamino, 5-methoxycarbonylmethylamino, 5-(1-methoxycarbonylpropylamino), 5-piperidin-1-yl and 5-pyrrol-1-yl analogs of the products listed in Examples 1-3, can be prepared, for example:

2-(pyrid-3-yl)-3-oxo-4-(3-trifluoromethylphenyl)-5-methoxymethylamono-2,3-dihydrofuran;
2-(N-methylpyrid-3-yl)-3-oxo-4-(3-trifluoromethyl-phenyl)-5-methoxymethylamino-2,3-dihydrofuran;
2-(pyrrolidin-1-yl)-3-oxo-4(3-trifluoromethylphenyl)-5-methoxymethylamino-2,3-dihydrofuran;
2-(pyrrolin-3-yl)-3-oxo-4-(3-trifluoromethylphenyl)-5-ethylthiomethylamino-2,3-dihydrofuran;
2-(pyrrol-3-yl)-3-oxo-4-(3-trifluoromethylphenyl)-5-ethylthiomethylamino-2,3-dihydrofuran;
2-(pyrrolidin-3-yl)-3-oxo-4-(3-trifluoromethylphenyl)-5-ethylthiomethylamino-2,3-dihydrofuran;
2-(pyrrol-1-yl)-3-oxo-4-(3-trifluoromethylphenyl)-5-ethylthiomethylamino-2,3-dihydrofuran;
2-(N-ethylpyrrol-3-yl)-3-oxo-4-(3-trifluoromethyl-phenyl)-5-ethylthiomethylamino-2,3-dihydrofuran;
2-(2-N-methylpyrrol-3-yl)-3-oxo-4-(3-trifluoromethyl-phenyl)-5-methoxycarbonylmethylamino-2,3-dihydrofuran;
2-(2H-pyrrol-3-yl)-3-oxo-4-(3-trifluoromethylphenyl)-5-methoxycarbonylmethylamino-2,3-dihydrofuran;
2-(4-piperidino)-3-oxo-4-(3-trifluoromethylphenyl)-5-methoxycarbonylmethylamino-2,3-dihydrofuran;
2-(1-piperidino)-3-oxo-4-(3-trifluoromethylphenyl)-5-methoxycarbonylmethylamino-2,3-dihydrofuran;
2-(N-methylpyrid-3-yl)-3-oxo-4-(3-trifluoromethyl-phenyl)-5-(1-methoxycarbonylprop-1-yl)amino-2,3-dihydrofuran;
2-(1H,4H-pyrid-3-yl)-3-oxo-4-(3-trifluoromethyl-phenyl)-5-(1-methoxycarbonylprop-1-yl)amino-2,3-dihydrofuran;
2-(1H,3H,4H-pyrid-3-yl)fluoro-3-oxo-4-(3-trifluoromethylphenyl)-5-(1-methoxycarbonylprop-1-yl)amino-2,3-dihydrofuran;
2-(pyrid-4-yl)-3-oxo-4-(3-trifluoromethylphenyl)-5-(1-methoxycarbonylprop-1-yl)amino-2,3-dihydrofuran;
2-(2H,5H-pyrid-3-yl)-3-oxo-4-(3-trifluoromethyl-phenyl)-5-(1-methoxycarbonylprop-1yl)amino-2,3-dihydrofuran;
2-(N-methyl-1-piperidino)-3-oxo-4-(3-trifluoromethyl-phenyl)-5-(1-methoxycarbonylprop-1-yl)amino-2,3-dihydrofuran;
2-(1H,4H,N-ethylpyrid-3-yl)-3-oxo-4-(3-trifluoromethylphenyl)-5-piperidin-1-yl-2,3-dihydrofuran;
2-(pyrid-3-yl)-3-oxo-4-(3-trifluoromethylphenyl)-5-pyrrol-1-yl-2,3-dihydrofuran;
2-(N-methylpyrrol-3-yl)-3-oxo-4-(3-trifluoromethyl-phenyl)-5-(2-pyrrolin-1-yl)-2,3-dihydrofuran;
2-(1H,4H,5H,6H-N-ethylpyrid-3yl)-3-oxo-4-(3-trifluoromethylphenyl)-5-(2-pyrrolin-1-yl)-1-yl-2,3-dihydrofuran;
2-(pyrid-3yl)-3-oxo-4-(3-trifluoromethylphenyl)-5-(piperidin-1-yl)-2,3-dihydrofuran;

2-(N-ethylpyrrol-3-yl)-3-oxo-4-(3-trifluoromethylphenyl)-5-(2-pyrrolin-1yl)-2,3-dihydrofuran; etc.

EXAMPLE 5

Lithium salt of 2-(pyrid-3-yl)-3-oxo-4-trifluoromethylphenyl)-5-methylamino-2,3-dihydrofuran ($R^1$=—$CH_3$, $R^2$=Li)

This example illustrates a preparation which can be used to prepare the lithium salts of the invention.

In this example, 5.4 ml of 1.6M n-butyllithium in hexane is added dropwise to a stirred solution containing 2.88 g of 2-(pyrid-3-yl)-3-oxo-4-(3-trifluoromethylphenyl)-5-amino-2,3-dihydrofuran in 25 ml of tetrahydrofuran at −30° C. The mixture is stirred for 20 minutes and can then be concentrated by evaporation in vacuo to yield the title compound.

Similarly, by applying this procedure, the corresponding lithium salts of the compounds of Examples 1 and 2 can be prepared.

EXAMPLE 6

The compounds listed in Table A hereinbelow were prepared using the appropriate starting materials and procedures described in the Examples set forth hereinabove.

pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 1.

POST-EMERGENT HERBICIDAL TEST

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 microgram/$gm^2$. After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity, 100 representing complete kill. The results of these tests are summarized in Table 2.

TABLE A

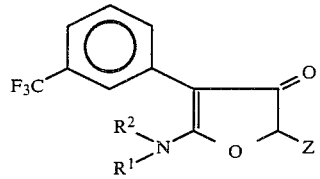

| | | | | ELEMENTAL ANALYSIS | | | | | |
|---|---|---|---|---|---|---|---|---|---|
| | | | | Carbon | | Hydrogen | | Nitrogen | |
| No. | $R^1$ | $R^2$ | Z | Calc. | Found | Calc. | Found | Calc. | Found | Melting Point °C. |
| 1 | H | H | pyrid-3-yl | 60.00 | 60.39 | 3.44 | 4.08 | 8.75 | 9.45 | 153–158 |
| 2 | $CH_3$ | H | pyrid-3-yl | 61.08 | 60.88 | 3.89 | 4.03 | 8.38 | 8.3 | 204–205* |
| C-1 | H | H | pyrid-2-yl | 60.00 | 60.76 | 3.44 | 3.84 | 8.75 | 8.64 | 219–221* |
| C-2 | $CH_3$ | H | pyrid-2-yl | 61.08 | 58.76 | 3.89 | 4.77 | 8.30 | 7.28 | oil |

* = Decomposition

EXAMPLE 7

In this example, the compounds of Table A were respectively tested using the procedures described hereinbelow for pre-emergent and post-emergent activity against a variety of grasses and broad-leaf plants including one grain crop and one broad-leaf crop. The compounds tested are identified by compound number in Table A hereinabove.

PRE-EMERGENT HERBICIDE TEST

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a non-ionic surfactant was added to the solution. 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface either at a dose of 27.5 micrograms/$gm^2$. The pot was watered and placed in a greenhouse. The

TABLE 1

Pre-Emergence Herbicidal Activity
Application Rate: 27.5 micrograms/$cm^2$,
unless otherwise noted

| | Broad-Leaf Plants % Phytotoxicity | | | | Grasses % Phytotoxicity | | | |
|---|---|---|---|---|---|---|---|---|
| Compound No. | Lambs-quarter | Mustard | Pigweed | Soybean | Crabgrass | Watergrass | Wild Oats | Rice |
| 1 | 100 | 100 | 100 | 75 | 98 | 70 | 45 | 70 |
| 2 | 100 | 100 | 100 | 35 | 100 | 94 | 94 | 65 |
| C-1 | 25 | 25 | 15 | 0 | 50 | 15 | 0 | 0 |
| C-2 | 20 | 20 | 0 | 0 | 20 | 20 | 0 | 0 |

TABLE 2

Post-Emergence Herbicidal Activity
Application Rate: 27.5 micrograms/$cm^2$,
unless otherwise noted

| | Broad-Leaf Plants % Phytotoxicity | | | | Grasses % Phytotoxicity | | | |
|---|---|---|---|---|---|---|---|---|
| Compound No. | Lambs-quarter | Mustard | Pigweed | Soybean | Crabgrass | Watergrass | Wild Oats | Rice |
| 1 | 50 | 85 | 40 | 35 | 10 | 0 | 0 | 0 |
| 2 | 40 | 65 | 55 | 70 | 60 | 40 | 70 | 20 |

TABLE 2-continued

Post-Emergence Herbicidal Activity
Application Rate: 27.5 micrograms/cm$^2$,
unless otherwise noted

| Com- | Broad-Leaf Plants % Phytotoxicity | | | | Grasses % Phytotoxicity | | | |
|---|---|---|---|---|---|---|---|---|
| pound No. | Lambs-quarter | Mus-tard | Pig-weed | Soy-bean | Crab-grass | Water-grass | Wild Oats | Rice |
| C-1 | 40 | 45 | 50 | 55 | 0 | 0 | 0 | 0 |
| C-2 | 60 | 70 | 70 | 40 | 0 | 0 | 0 | 0 |

As can be seen from the above Table 1, the test compounds Nos. 1 and 2 of the invention exhibited a broad spectrum of very good pre-emergence phytotoxic activity especially against broad-leaf plants. As shown in Table 2 the compounds also exhibit a broad spectrum of moderate post-emergence phytotoxic activity against broad-leaf plants. In contrast to this, the two-position isomer comparison compounds exhibited very poor pre-emergence herbicidal activity and at best only comparable post-herbicidal activity.

Obviously, many modifications and variations of the invention described hereinabove and below can be made without departing from the essence and scope thereof.

What is claimed is:

1. A compound having the formula:

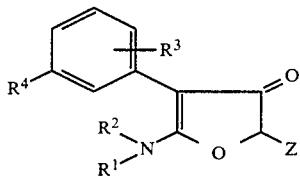

wherein
R$^1$ is hydrogen or alkyl having 1 through 4 carbon atoms;
R$^2$ is hydrogen, alkyl having 1 through 4 carbon atoms, alkenyl having 3 or 4 carbon atoms, lower alkoxycarbonylalkyl having 1 through 4 carbon atoms in the alkoxy moiety and 1 through 4 carbon atoms in the alkyl moiety, lower alkoxyalkyl wherein the alkoxy and alkyl moieties independently have 1 through 3 carbon atoms, or lower alkylthioalkyl wherein the alkyl moieties independently have 1 through 3 carbon atoms; or
R$^1$ and R$^2$ together with the nitrogen atom to which they are joined form a saturated nitrogen heterocycle having 3 through 6 carbon atoms one of which is the joining nitrogen atom and the remainder are carbon atoms or unsaturated heterocycle selected from the group of 2-pyrrolin-1-yl; 3-pyrrolin-1-yl; 1,2,3,4-tetrahydropyrid-1-yl or 1,2,5,6-tetrahydropyrid-1-yl;
R$^3$ is hydrogen, lower alkyl, lower alkoxy, halo, or trifluoromethyl and can be set at any available position on the phenyl ring;
R$^4$ is lower alkyl, lower alkoxy, halo, lower haloalkyl having 1 through 4 carbon atoms and 1 through 4 carbon atoms and 1 through 3 of the same or different halo atoms, lower haloalkoxy having 1 through 4 carbon atoms and 1 through 3 of the same or different halo atoms, or lower haloalkylthio having 1 through 4 carbon atoms and 1 through 3 of the same or different halo atoms; and Z is a saturated or unsaturated nitrogen heterocycle radical having 6-ring atoms one of which ring atoms is nitrogen and the remainder of said ring atoms are carbon atoms; or a saturated or unsaturated substituted nitrogen heterocycle having 6-ring atoms one of which is nitrogen and the remainder of which are carbon atoms and wherein said nitrogen atom is substituted with a methyl or ethyl group; with the proviso that said nitrogen heterocycle and said substituted heterocycle are not attached to the furan moiety of Formula I via the 2-position of said nitrogen heterocycle;
or a compatible cation salt thereof.

2. The compound of claim 1 wherein R$^1$ and R$^2$ are independently selected from the group of hydrogen, methyl or ethyl.

3. The compound of claim 2 wherein one of R$^1$ or R$^2$ is hydrogen and the other is hydrogen, methyl or ethyl.

4. The compound of claim 1 wherein R$^3$ is hydrogen.

5. The compound of claim 2 wherein R$^3$ is hydrogen.

6. The compound of claim 3 wherein R$^3$ is hydrogen.

7. The compound of claim 1 wherein Z is an unsaturated heterocycle radical.

8. The compound of claim 1 wherein Z is a saturated heterocycle radical.

9. The compound of claim 1 werein Z is selected from the group of pyrid-3-yl, and N-methylpyrid-3-yl.

10. The compound of claim 6 wherein Z is pyrid-3-yl.

11. The compound of claim 1 wherein said compound is selected from the group having the formula:

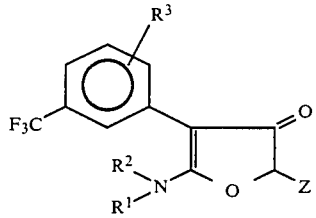

wherein R$^1$, R$^2$, R$^3$ and Z are as defined in claim 1; or a compatible cation salt thereof.

12. The compound of claim 11 wherein R$^1$ and R$^2$ are independently hydrogen, methyl or ethyl.

13. The compound of claim 12 wherein one of R$^1$ or R$^2$ is hydrogen and the other is hydrogen, methyl or ethyl and compatible cation salts thereof.

14. The compound of claim 14 wherein Z is pyrid-3-yl.

15. The compound of claim 13 wherein Z is selected from the group of pyrid-3-yl and N-methylpyrid-3-yl.

16. The compound of claim 11 wherein R$^3$ is hydrogen.

17. The compound of claim 13 wherein R$^3$ is hydrogen.

18. The compound of claim 17 wherein Z is pyrid-3-yl.

19. The compound of claim 18 wherein one of R$^1$ or R$^2$ is hydrogen and the other is methyl or ethyl.

20. The compound of claim 18 wherein R$^1$ and R$^2$ are each hydrogen.

21. The compound of claim 14 wherein R$^3$ is hydrogen, and one of R$^1$ or R$^2$ is hydrogen and the other is methyl.

22. The compound of claim 1 wherein the Z heterocycle is not attached to the furan nucleus via its ring nitrogen atom.

23. The compound of claim 1 wherein $R^1$ is hydrogen or alkyl and $R^2$ is hydrogen, alkyl, alkenyl, lower alkoxycarbonylalkyl, lower alkoxyalkyl or lower alkylthioalkyl.

24. The compound of claim 11 wherein $R^1$ is hydrogen or alkyl and $R^2$ is hydrogen, alkyl, alkenyl, lower alkoxycarbonylalkyl, lower alkoxyalkyl or lower alkylthioalkyl.

25. A herbicidal composition comprising a herbicidally effective amount of the compound of claim 1, or mixtures thereof, and a compatible carrier.

26. A method for controlling undesired plants which comprises applying a herbicidally effective amount of the compound of claim 1, or mixtures thereof, to the foilage or potential growth medium of said plants.

27. A method for controlling undesired plants which comprises applying a herbicidally effective amount of the compound of claim 21, or mixtures thereof, to the foilage or potential growth medium of said plants.

28. A plant growth regulating composition which comprises an amount of the compound of claim 1, or mixtures thereof, effective to alter the growth pattern of plants.

29. A method for regulating the growth of plants which comprises applying to the foilage of said plants or their growth medium an amount of the compound of claim 1, or mixtures thereof, effective to alter the growth pattern of such plants.

* * * * *